United States Patent [19]
Flockenhaus et al.

[11] Patent Number: 4,539,016
[45] Date of Patent: Sep. 3, 1985

[54] METHOD OF AND APPARATUS FOR ADJUSTING AND MAINTAINING CONSTANT THE TEMPERATURE DURING METHANIZING OF A CHARGE GAS

[75] Inventors: Claus Flockenhaus, Essen; Erich Hackler, Kettwig; Werner Lommerzheim, Mülheim, all of Fed. Rep. of Germany

[73] Assignees: Thyssengas G.m.b.H., Duisburg-Hamborn; Didier Engineering, Essen, both of Fed. Rep. of Germany

[21] Appl. No.: 257,352

[22] Filed: Apr. 24, 1981

Related U.S. Application Data

[63] Continuation of Ser. No. 68,490, Aug. 21, 1979, abandoned, which is a continuation of Ser. No. 847,550, Nov. 1, 1977, abandoned.

[30] Foreign Application Priority Data

Nov. 12, 1976 [DE] Fed. Rep. of Germany ....... 2651567

[51] Int. Cl.³ .................................... C10K 3/04
[52] U.S. Cl. .................................... 48/197 R; 48/210; 518/702; 518/704; 518/705; 48/712; 518/714
[58] Field of Search ........ 48/197 R, 62 R, 210, 48/214 R, 214 H; 122/40, 146; 165/104.16; 518/703, 2, 702, 704, 705, 714

[56] References Cited

U.S. PATENT DOCUMENTS 3,975,169 8/1976 Gent .
3,977,843 8/1976 Dew et al. .

FOREIGN PATENT DOCUMENTS 339745 5/1972 U.S.S.R. ............................. 122/4 D

OTHER PUBLICATIONS

"Survey of Methanation Chem. and Processes", Seglin et al., Methanation of Syn Gas, Aeglin, Advances in Chemistry, pp. 1, 19-27, 1975.
Encyclopedia of Chem. Tech., Kirk-Othmer, vol. 4, pp. 446, 447, 477-480, 2nd Ed., 1964.
Fluidization, Othmer, pp. 130-133, Reinhold Publishing Co. 1956.

Primary Examiner—Peter Kratz
Attorney, Agent, or Firm—Toren, McGeady, Stanger, Goldberg & Kiel

[57] ABSTRACT

In methanizing CO and $H_2$ containing charge gases, the charge gas is passed upwardly through a vertically extending fluidized bed reactor flowing, in turn, through a fluidized bed zone, a dust bed zone and a separation zone. From the separation zone, the gas is conveyed out of the reactor to a point of use. Coolant tubes are positioned in the reactor passing vertically through the fluidized bed zone, the dust bed zone and the separation zone for removing the heat generated in the reaction. An evaporable coolant, preferably water, is circulated through the coolant tubes. In a separate steam drum, the vapor pressure of the coolant is set for maintaining constant the temperature of the vaporizing coolant.

6 Claims, 1 Drawing Figure

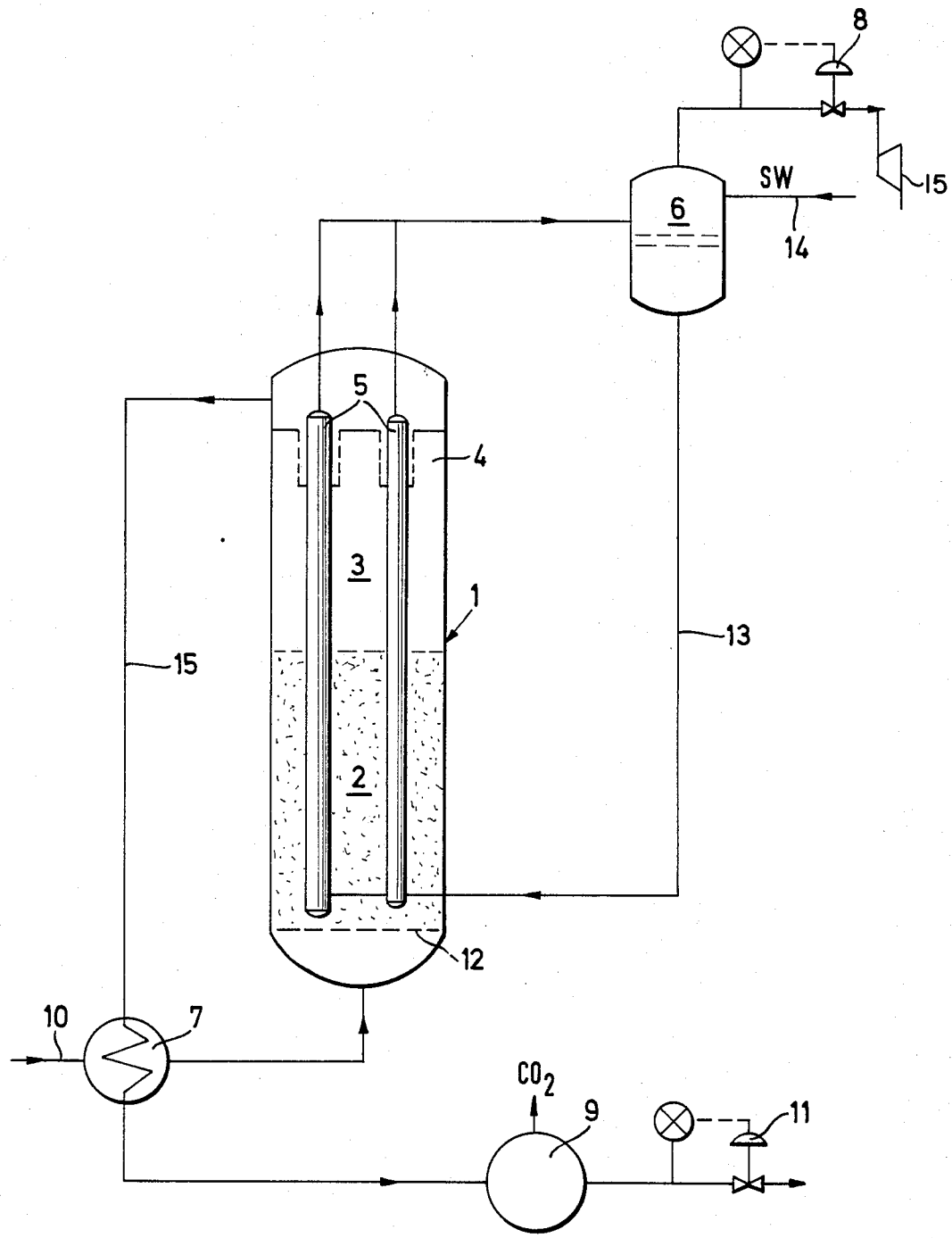

METHOD OF AND APPARATUS FOR ADJUSTING AND MAINTAINING CONSTANT THE TEMPERATURE DURING METHANIZING OF A CHARGE GAS

This is a continuation of application Ser. No. 068,490 filed Aug. 21, 1979 which in turn was a continuation of application Ser. No. 847,550 filed Nov. 1, 1977 both abandoned.

SUMMARY OF THE INVENTION

This invention relates to a method for adjusting and keeping constant the temperature in methanizing of CO- and $H_2$- containing charge gas in a fluidized bed reactor comprising a fluidized bed zone and a dust bed zone, wherein the charge gas is reacted on a fluidized bed catalyst and the reaction heat is removed by means of an evaporating coolant, and also to a device for carrying out this method.

A method of this general type with an associate device is known from German Offenlegungsschrift No. 2,449,587; it operates at a temperature of 288° to 565° C. and a pressure of 35 to 140 bars with various catalysts, for example chromium oxide, molybdenum oxide, iron oxide or molybdenum sulphide. The fluidized bed temperature must therefore be set and maintained according to the particular charge gas and fluidized bed catalyst, in order to attain a maximum methane yield and to operate as far as possible at the theoretical equilibrium temperature. In the known method, the reaction heat is removed by an evaporating coolant, flowing through cooling pipe loops disposed in the reaction zone of the fluidized bed reactor. It is not possible in this way alone, however, to adjust the fluidized bed temperature with sufficient accuracy and to modify it with sensitivity.

Therefore, the task underlying the present invention is to create a method and a device for methanizing, wherein the temperature of the fluidized bed is maintained by simple means at an accurately adjustable level and the gas throughput can thus be brought close to the theoretical heterogeneous gas equilibrium corresponding to the set temperature.

This task is achieved in that the boiling temperature of the evaporating coolant is set via its vapor pressure. Water is especially suitable as evaporating coolant.

The boiling temperature can be set to about 60° to 80° C. below the desired fluidized bed temperature. If the boiling temperature, for example, on the water side is maintained at 260° C. (about 48 bars steam pressure), then the fluidized bed temperature is about 330° C.

The reaction heat should be removed both in the fluidized bed zone and also in the dust bed zone situated above it. Since the powdered catalyst is present as a cloud of powder in the dust bed zone, the dust bed zone can be utilized for the methanization. Although the reaction heat has already been for the greater part removed in the fluidized bed zone, residual gas reactions still take place in the dust bed zone on the finely divided catalyst. The heat production from this gas reaction is, however, less and the temperature of the dust bed zone is about 10° lower than that of the fluidized bed zone.

The catalyst dust is separated from the gas in a separation zone. In this separation zone, the gas comes intensively into contact with the catalyst dust and is still further after-methanized at a correspondingly low temperature. To render this possible, a still lower temperature should exist in the separation zone than in the dust bed zone.

The method according to the present invention is preferably carried out at high pressure. An economical pressure can be between about 6 and 100 bars.

If the gas produced, after partial washing out of the $CO_2$, is to be used as a substitute for mains natural gas, then the operating pressure is set at about 30 to 60 bars, to suit the distribution grid, in order to save a subsequent compressor stage.

The steam from the cooling system can be utilized in expansion turbines.

Gases containing CO and $H_2$ from autothermal or steam cracking plants for hydrocarbons are suitable as charge gases for the process. The gases produced by recent methods utilizing nuclear energy from coal and brown coal can also be used in their desulphurized condition.

A device for carrying out the method of this invention consists of a fluidized bed reactor, containing a fluidized bed catalyst and receiving the charge gases, comprising a fluidized bed zone and a dust bed zone and a cooler for removing the reaction heat. The cooler is characterized in that it operates on the coolant side as an evaporator and possesses a steam pressure control, which causes the coolant steam to overflow at a specific pressure and thus regulates the boiling temperature of the coolant to a specific level. An expansion turbine is preferably connected downstream of the evaporator. The cooler may comprise boiler tubes extending vertically through the fluidized bed reactor. The cooling device is situated in the fluidized bed zone and optionally also in the dust bed zone. If the apparatus possesses, in a known manner, a separation zone for the entrained powdered fluidized bed catalyst, a cooler may also be situated in the separation zone.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there is illustrated and described a preferred embodiment of the invention.

BRIEF DESCRIPTION OF THE DRAWING

The drawing is a diagrammatic representation of the present invention.

DETAILED DESCRIPTION OF THE INVENTION

The charge gas enters a fluidized bed reactor 1, in the form of a vertically elongated tank, from below through a charge gas line 10 via a heat exchanger 7. The charge gas is introduced, uniformly distributed by means of an outlet floor 12 in the lower part of the tank into the fluidized bed zone 2 situated above this floor and containing a powdered catalyst. As the methanizing reaction proceeds, the charge gas flows upwardly into a dust bed zone 3 and thereby entrains a portion of the powdered fluidized bed catalyst with it, so that a catalyst cloud is produced in the dust bed zone. The dust bed zone 3 continues at the top into a separation zone 4, in which the powdered fluidized bed catalyst is separated from the gas. Boiler tubes 5 extend vertically through the fluidized bed reactor 1, and pass through the fluidized bed zone 2, the dust zone 3 and the separation zone 4.

The reaction heat produced in the conversion of the charge gas is removed by means of the boiler tubes which contain an evaporating coolant, the boiling temperature of which is maintained at a specific value by adjusting the vapor pressure. This is effected by connecting the boiler tubes 5 by means of a circuit pipe to a steam drum 6, to the steam space of which a pressure regulator 8 is connected which, when a specific pressure is exceeded, allows steam to overflow. Steam flowing past the pressure regulator 8 is conveyed into an expansion turbine 15. Make-up water is supplied to the pressure regulator 9 through a water line 14.

The gas methanized in the fluidized bed reactor is removed from the upper region of the fluidized bed reactor 1 by a gas line 15 and after passing through the heat exchanger 7 flows into a $CO_2$-washing plant 9. From the washing plant the gas is conveyed as mains natural gas through a pressure regulator 11 to the consumer grid.

While a specific embodiment of the invention has been shown and described in detail to illustrate the application of the inventive principles, it will be understood that the invention may be embodied otherwise without departing from such principles.

What is claimed is:

1. Method for methanizing charge gases containing CO and $H_2$ in a fluidized bed reactor containing an upwardly extending fluidized bed zone containing a powdered catalyst and a separation zone located above the fluidized bed zone, flowing the charge gases upwardly through the fluidized bed zone from the lower end thereof and reacting the charge gases with the powdered catalyst in the fluidized bed, removing the heat generated in the reaction by an evaporating coolant and passing the evaporating coolant through the fluidized bed zone in indirect heat transfer relation with the powdered catalyst therein, adjusting the vapor pressure of the coolant before introducing it into the fluidized bed zone for maintaining a desired boiling temperature of the coolant in the fluidized bed zone, wherein the improvement comprises, maintaining an upwardly extending dust bed zone within the reactor between the upper end of the fluidized bed zone and the separation zone in the fluidized bed reactor with the powdered catalyst being present in the upwardly flowing charge gases in the dust bed zone as a cloud of powdered catalyst, reacting the charge gases with the cloud of powdered catalyst in the dust bed zone, separating the powdered catalyst from the charge gas within the separation zone whereby the separation step is completely effected within the reactor, removing the heat generated in the reaction from the dust bed zone and from the separation zone by flowing the evaporating coolant from the fluidized bed zone in indirect heat transfer relation serially through the cloud of powdered catalyst in the dust bed zone and then the separation zone, maintaining the temperature of the evaporating coolant in the range of 60° to 80° C. below the temperature in the fluidized bed zone and in a corresponding range of 50° to 70° C. below the temperature in the dust bed zone with the pressure of the evaporating coolant being adjusted for establishing the boiling temperature of the coolant.

2. In methanizing CO and $H_2$ containing charge gases, as set forth in claim 1, comprising desulphurizing charge gases obtained from coal and brown coal before introducing the charge gases into the fluidized bed zone.

3. In methanizing CO and $H_2$ containing charge gases, as set forth in claim 1, comprising maintaining the operating pressure of the charge gases in the range of 6 to 100 bars.

4. In methanizing CO and $H_2$ containing charge gases, as set forth in claim 3, comprising maintaining the operating pressure of the charge gas in the range of 30 to 60 bars.

5. In methanizing CO and $H_2$ containing charge gases, as set forth in claim 1, including the step of using water as the evaporating coolant and utilizing the steam produced in the methanizing process in expansion turbines.

6. In methanizing CO and $H_2$ containing charge gases, as set forth in claim 1, comprising conveying the charge gas used in the fluidized bed reactor from autothermal or steam cracking plants for hydrocarbons.

* * * * *